US010045535B2

(12) United States Patent
Andersch et al.

(10) Patent No.: US 10,045,535 B2
(45) Date of Patent: *Aug. 14, 2018

(54) ACTIVE SUBSTANCE COMBINATION BASED ON TRIFLUOROBUTINYL COMPOUNDS AND EXHIBITING NEMATICIDAL AND INSECTICIDAL PROPERTIES

(71) Applicant: ADAMA MAKHTESHIM LTD., Beer Sheva (IL)

(72) Inventors: Wolfram Andersch, Bergisch Gladbach (DE); Anton Kraus, Leichlingen (DE); Koichi Ishikawa, Tochigi (JP)

(73) Assignee: ADAMA MAKHTESHIM LTD., Beer-Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/484,410

(22) Filed: Apr. 11, 2017

(65) Prior Publication Data
US 2017/0215423 A1 Aug. 3, 2017

Related U.S. Application Data

(62) Division of application No. 14/339,904, filed on Jul. 24, 2014, now Pat. No. 9,681,662, which is a division of application No. 10/555,105, filed as application No. PCT/EP2004/004167 on Apr. 20, 2004, now Pat. No. 8,815,921.

(30) Foreign Application Priority Data

May 2, 2003 (DE) .................. 103 19 590

(51) Int. Cl.
A61K 31/426 (2006.01)
A01N 43/78 (2006.01)
A01N 43/56 (2006.01)
A01N 47/06 (2006.01)
A01N 47/24 (2006.01)
A01N 47/44 (2006.01)
A01N 53/00 (2006.01)
A01N 57/16 (2006.01)
A01N 47/02 (2006.01)
A01N 51/00 (2006.01)

(52) U.S. Cl.
CPC ............ A01N 43/78 (2013.01); A01N 43/56 (2013.01); A01N 47/02 (2013.01); A01N 47/06 (2013.01); A01N 47/24 (2013.01); A01N 47/44 (2013.01); A01N 51/00 (2013.01); A01N 53/00 (2013.01); A01N 57/16 (2013.01); A61K 31/426 (2013.01)

(58) Field of Classification Search
CPC .................................................. A01N 43/78
See application file for complete search history.

(56) References Cited

U.S. PATENT DOCUMENTS

| 2,758,115 | A | 8/1956 | Lorenz |
| 3,058,990 | A | 10/1962 | Harman |
| 3,264,177 | A | 8/1966 | Kenaga |
| 3,309,266 | A | 3/1967 | Magee |
| 3,513,172 | A | 5/1970 | Brokke |
| 4,748,186 | A | 5/1988 | Cullen et al. |
| 6,277,791 | B1 | 8/2001 | Assmann et al. |
| 6,300,348 | B1 | 10/2001 | Sirinyan et al. |
| 6,734,198 | B1 | 5/2004 | Watanabe et al. |
| 6,743,814 | B2 | 6/2004 | Watanabe et al. |
| 7,078,527 | B2 | 7/2006 | Straub |
| 7,385,093 | B2 | 6/2008 | Straub |
| 7,439,408 | B2 | 10/2008 | Straub |
| 8,815,921 | B2 * | 8/2014 | Andersch ............... A01N 43/78 514/369 |
| 9,681,662 | B2 * | 6/2017 | Andersch ............... A01N 43/78 |
| 2006/0004196 | A1 | 1/2006 | Straub |
| 2006/0173190 | A1 | 8/2006 | Wantanabe et al. |
| 2007/0155706 | A1 | 7/2007 | Andersch et al. |
| 2008/0274885 | A1 | 11/2008 | Martin et al. |
| 2009/0111759 | A1 | 4/2009 | Pedersen et al. |
| 2017/0006872 | A1 | 1/2017 | Sakamoto |

FOREIGN PATENT DOCUMENTS

| AU | 2004233566 A1 | 11/2004 |
| CN | 1476437 A | 2/2004 |
| DE | 2641343 | 4/1977 |
| EP | 0210487 A1 | 2/1987 |
| EP | 0234045 A2 | 9/1987 |
| EP | 0347488 A1 | 12/1989 |
| EP | 2604118 A1 | 6/2013 |
| GB | 1181657 | 2/1970 |
| JP | 2003-503485 | 1/2003 |
| WO | 8607590 A1 | 12/1986 |
| WO | 9215555 A2 | 9/1992 |
| WO | 93/10083 A1 | 5/1993 |
| WO | 93/22297 A1 | 11/1993 |
| WO | 9524403 A1 | 9/1995 |
| WO | 01/02378 A1 | 1/2001 |

(Continued)

OTHER PUBLICATIONS

The e-Pesticide Manual, 15th edition, version 5.0, British Crop Protection Council, 2009-2010; relevant entries/passages for spinosad, abamectin and emamectin-benzoate; downloaded Jan. 26, 2017.
Spinosad pages downloaded Feb. 2, 2017, from http://research.omicsgroup.org/index.php/Spinosad.
Classification of insecticides downloaded Feb. 2, 2017, from www.alanwood.net/pesticides/class.insecticides.

(Continued)

Primary Examiner — Paul V Ward
(74) Attorney, Agent, or Firm — Browdy and Neimark, PLLC

(57) ABSTRACT

The invention relates to novel active substance combinations consisting of heterocyclic trifluorobutenylen of formula (1), wherein X is halogen and n is 0, 1 or 2, and of known insecticide substances. Said novel active substance combinations are suitable for fighting harmful pests like insects and nematodes.

7 Claims, No Drawings

(56) References Cited

FOREIGN PATENT DOCUMENTS

| WO | 2001/02378 |    | 1/2001  |
|----|------------|----|---------|
| WO | 03/029231  |    | 4/2003  |
| WO | 03/029231  | A1 | 4/2003  |
| WO | 03059896   | A1 | 7/2003  |
| WO | 2004005268 | A1 | 1/2004  |
| WO | 2004095929 | A1 | 11/2004 |
| WO | 20050003107| A1 | 1/2005  |
| WO | 2007/089455| A1 | 8/2007  |
| WO | 2013107795 | A2 | 7/2013  |
| WO | 2015115446 | A1 | 8/2015  |
| WO | 2016042557 | A1 | 3/2016  |

OTHER PUBLICATIONS

IRAC, Mode of Action Classification, Poster Edition 3, Feb. 2012, www.irac-online.org.

IRAC MoA Classification Scheme, Version 7.2, Apr. 2012, pp. 1-23, www.irac-online.org.

AU Official Action dated May 1, 2008 (AU App. No. 2004233566).

AU Official Action dated Nov. 11, 2009 (AU App. No. 2004233566).

The Carlton Savings Co. Ltd., re Appl. No. AU 20,769/67; Comm'r Patents, vol. 34, No. 14, p. 1404 (Australia).

Beecham Group Ltd's (Amoxycillin) Application, Ct. of Appl. AU, 1980 R.P.C. No. 10 (1980) pp. 261-304.

In re I.G. Farbenindustrie A.G.'s Patents, High Court Just. (Chancery Div.) vol. XLVII, No. 9, (1930) pp. 389-334.

E. I. DuPont de Nemours & Co. (Witsiepe) Application, House of Lords, Fleet Street Reports (1982), pp. 303-316.

Examiner report in corresponding AU Application No. 2004233565, dated Jun. 2, 2009.

S.R. Colby "Calculating Synergistic and Antagonistic Reponses of Herbicide Combinations," WEEDS 15 (1967). pp. 20-22.

Yuji Oka, et al, Nematicidal efficacy of MCW-2, a new nematicide of the fluoroalkenyl group, against the root-knot nematode Meloidogyne javanica Pest Manag Sci 65; 1082-1 089; 2009.

Laura L. Van Eerd, Pesticide metabolism in plants and microorganisms, 51:472-495, Weed Science (2003).

\* cited by examiner

ACTIVE SUBSTANCE COMBINATION BASED ON TRIFLUOROBUTINYL COMPOUNDS AND EXHIBITING NEMATICIDAL AND INSECTICIDAL PROPERTIES

The present invention relates to novel active compound combinations comprising, firstly, known heterocyclic trifluorobutenylenes and, secondly, known insecticidally active compounds, which combinations are highly suitable for controlling animal pests, such as insects and nematodes.

It is already known that certain heterocyclic trifluorobutenylenes have nematicidal properties (WO 01/02378 A1). An activity of these compounds against insects has not been reported. It has now been found that certain heterocyclic trifluorobutenylenes also have insecticidal action. This action is good, but not entirely satisfactory.

It is also known that numerous phosphoric esters, carbamates, heterocycles, organotin compounds, benzoylureas and pyrethroids have insecticidal and acaricidal properties (cf., for example, U.S. Pat. No. 2,758,115, U.S. Pat. No. 3,309,266, GB 1,181,657, WO 93/22297 A1, WO 93/10083 A1, DE 26 41 343 A1, EP 347 488 A1, EP 210 487 A1, U.S. Pat. No. 3,264,177 and EP 234 045 A2). However, the action of these compounds is likewise not entirely satisfactory.

It has now been found that the novel active compound combinations comprising at least one compound of the formula (I)

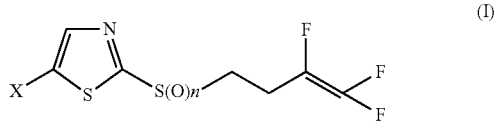

in which
X represents halogen and
n represents 0, 1 or 2,
"active compounds of group 1")
and
at least one active compound from the following group of active compounds abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R isomers, alpha-cypermethrin (alphamethrin), amidoflumet, aminocarb, amitraz, avermectin, AZ-60541, aza-dirachtin, azamethiphos, azinphos-methyl, azinphos-ethyl, azocyclotin, *Bacillus popilliae*, *Bacillus sphaericus*, *Bacillus subtilis*, *Bacillus thuringiensis*, *Bacillus thuringiensis* strain EG-2348, *Bacillus thuringiensis* strain GC-91, *Bacillus thuringiensis* strain NCTC-11821, baculoviruses, *Beauveria bassiana*, *Beauveria tenella*, benclothiaz, bendiocarb, benfuracarb, bensultap, benz-oximate, beta-cyfluthrin, beta-cypermethrin, bifenazate, bifenthrin, binapacryl, bioallethrin, bio-allethrin-S-cyclopentyl isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfen-vinphos, chlorfluazuron, chlormephos, chlorbenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella* granuloviruses, cyfluthrin, cyhalothrin, cyhexatin, cypermethrin, cyphenothrin (1R-trans isomer), cyromazine, DDT, deltamethrin, demeton-S-methyl, demeton-S-methylsulfone, diafenthiuron, di-alifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfo-ton, docusat-sodium, dofenapyn, DOWCO-439, eflusilanate, emamectin, emamectin-benzoate, em-penthrin (1R isomer), endosulfan, entomopthora spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granuloviruses, halfenprox, halofeno-zide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclearpolyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae*, *Metharhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700, mono-crotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, *Paecilomyces fumosoroseus*, parathion-methyl, parathion (-ethyl), permethrin (cis-, trans-), petroleum, PH-6045, phenothrin (1R trans isomer), phenthoate, phorate, phosalone, phosmet, phosphamidon, phosphocarb, phoxim, piperonyl butoxide, pirimi-carb, pirimiphos-methyl, pirimiphos-ethyl, pralethrin, profenofos, profluthrin, promecarb, propa-phos, propargite, propetamphos, propoxur, prothiofos, prothoate, protrifenbute, pymetrozine, pyra-clofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfo-tep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R isomer), tetrasul, theta-cypermethrin, thiacloprid, thiamethoxam, thiapronil, thia-triphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, tri-azophos, triazuron, trichlophenidine, trichlorfon, triflumuron, trimethacarb, vamidothion, vaniliprole, verbutin, *Verticillium lecanii*, WL-108477, WL-40027, YI-5201, YI-5301, YI-5302, XMC, xylylcarb, ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf. WO-96/37494, WO-98/25923) and the compound of the formula (IIA)

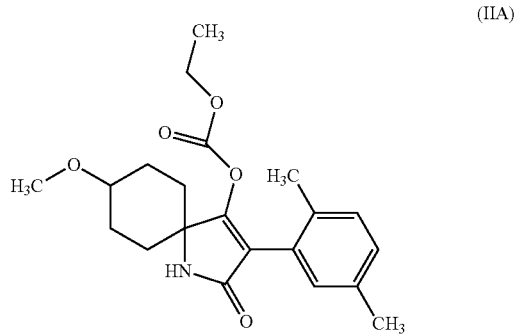

(carboxylic acid, 3-(2,5-dimethylphenyl)-8-methoxy-2-oxo-1-azaspiro[4.5]dec-3-en-4-yl ethyl ester, (9Cl))

("active compounds of group 2")

have very good nematicidal, insecticidal and acaricidal properties.

Surprisingly, the nematicidal, insecticidal and/or acaricidal action of the active compound combinations according to the invention is considerably higher than the sum of the actions of the individual active compounds. Thus, an unforeseeable synergistic effect is present, and not just in addition of actions.

In addition to at least one active compound of the formula (I), the active compound combinations according to the invention comprise at least one active compound of group 2.

The active compounds of group 2 can be divided into the following different classes of substances, for example:

Benzisothiazoles, such as, for example, benclothiaz; benzoylureas, such as, for example, bistrifluron, chlorfluazuron, diflubenzuron, DOWCO-439, fluazuron, flucycloxuron, flufenoxuron, hexaflumuron, lufenuron, novaluron, noviflumuron, teflubenzuron, triflumuron; biological insecticides, such as, for example, ABG-9008, *Bacillus popilliae, Bacillus sphaericus, Bacillus subtilis, Bacillus thuringiensis, Bacillus thuringiensis* strain EG-2348, *Bacillus thuringiensis* strain NCTC-11821, *Bacillus thuringiensis* strain GC-91, baculoviruses, *Beauveria bassiana, Beauveria tenella, Cydia pomonella* granuloviruses (CpGV), entomophthora spp., granuloviruses, nuclear polyhedrosis viruses, *Metharhizium anisopliae, Metharhizium flavoviride, Paecilomyces fumosoroseus, Verticillium lecanii*; carbamates, such as, for example, alanycarb, aldicarb, aldoxycarb, aminocarb, bendiocarb, benfuracarb, BPMC, bufencarb, butocarboxim, carbaryl, carbofuran, carbosulfan, cloethocarb, ethiofencarb, fenobucarb, fenoxycarb, furathiocarb, isoprocarb, metam-sodium, methiocarb, methomyl, metolcarb, metolcarb, oxamyl, phosphocarb, pirimicarb, promecarb, propoxur, thiodicarb, thiofanox, trimethacarb, XMC, xylylcarb; dinitrophenols, such as, for example, binapacryl, dinobuton, dinocap; diphenyl ethers, such as, for example, difenolan, dofenapyn, pyriproxyfen; esters, such as, for example, cycloprene, gossyplure, hydroprene, kinoprene, methoprene, docusat-sodium, spirodiclofen, spiromesifen; indenooxadiazinecarboxamides, such as, for example, indoxacarb; macrolides, such as, for example, abamectin, avermectin, emamectin, emamectin-benzoate, ivermectin, milbemectin, milbemycin, moxidectin, spinosad, thuringiensin; neonicotinoids, such as, for example, acetamiprid, AKD 1022, clothianidin, dinetofuran, imidacloprid, nitenpyram, thiacloprid, thiamethoxam; phosphates, such as, for example, bromfenvinfos (-methyl), chlorfenvinphos, dichlorvos, dicrotophos, dimethylvinphos, heptenophos, mevinphos, monocrotophos, naled, phosphamidon, propaphos, temivinphos, tetrachlorvinphos; phosphoramidates, such as, for example, fenamiphos, isofenphos; phosphoramidothioates, such as, for example, acephate, methamidophos, propetamphos; phthalamides, such as, for example, N2-[1,1-dimethyl-2-(methylsulfonyl)ethyl]-3-iodo-N1-[2-methyl-4-1,2,2,2-tetrafluoro-1-(trifluoromethyl)ethyl]phenyl-1,2-benzenedicarboxamide (CAS Reg. No. 272451-65-7, cf. EP 0 919 542 A2), pyrazoles, such as, for example, acetoprole, ethiprole, fenpyroximate, fipronil, vaniliprole; pyrazolecarboxamides, such as, for example, fenyprad, tebufenpyrad, tolfenpyrad; pyrethroids and pyrethroid analogs, such as, for example, resmethrin, acrinathrin, allethrin (1R isomer), alpha-cypermethrin, beta-, cyfluthrin, beta-cypermethrin, bifenthrin, bioallethrin, bioallethrin (S-cyclopentyl isomer), bioethanomethrin, biopermethrin, bioresmethrin, brofenprox, chloethocarb, chlovaporthrin, cis-cypermethrin, cis-resmethrin, clocythrin, cycloprothrin, cyfluthrin, cyhalothrin, cypermethrin, cyphenothrin (1R-trans isomer), deltamethrin, dimefluthrin, eflusilanate, empenthrin (1R isomer), esfenvalerate, etofenprox, fenfluthrin, fenpropathrin, fenpyrithrin, fenvalerate, flubrocythrinate, flubrocythrinate, flucythrinate, flufenprox, flufenprox, flumethrin, fluvalinate, fubfenprox, gamma-cyhalothrin, halfenprox, imiprothrin, kadethrin, lambda-cyhalothrin, metofluthrin, MIT-800, permethrin, phenothrin (1R-trans isomer), prallethrin, profluthrin, protrifenbute, pyresmethrin, pyrethrum, RU-12457, RU-15525, silafluofen, tau-fluvalinate, tefluthrin, tetramethrin (1R isomer), theta-cypermethrin, tralocythrin, tralomethrin, transfluthrin, zeta-cypermethrin; pyridazinones, such as, for example, butylpyridaben, NC-170, NC-184, NC-194, NC-196, pyridaben, pyridaphenthion, pyridathion; pyrroles, such as, for example, chlorfenapyr; quinazolines, such as, for example, fenazaquin; thiophosphates and dithiophosphates, such as, for example, azamethiphos, azinphos-ethyl, azinphos-methyl, bromophos-ethyl, butathiofos, cadusafos, carbophenothion, chlorethoxyfos, chlormephos, chlorpyrifos, chlorpyrifos, chlorpyrifos-ethyl, chlorpyrifos-methyl, coumaphos, cyanophos, demeton, demeton-S-methyl, demeton-S-methyl-sulfone, dialifos, diazinon, dichlofenthion, dimethoate, disulfoton, ethion, ethoprophos, etrimfos, fenitrothion, fensulfothion, fenthion, flupyrazofos, fonofos, formothion, fosmethilan, iodofenphos, iprobenfos, isazofos, isoxathion, malathion, mecarbam, mesulfenfos, methacrifos, methidathion, omethoate, oxydemeton-methyl, parathion-methyl, phenthoate, phorate, phosalone, phosmet, phosphocarb, phoxim, pirimiphos-ethyl, pirimiphos-, methyl, profenofos, prothiofos, prothoate, pyraclofos, pyridaphenthion, pyridathion, quinalphos, sulfotep, sulprofos, tebuprimifos, temephos, terbufos, thiatriphos, thiometon, triazophos, vamidothion; thiophosphonates, such as, for example, cyanofenphos, EPN, fosthiazate; thiosulfonates, such as, for example, bensultap, thiosultap-sodium; thioureas, such as, for example, diafenthiuron; triazines, such as, for example, cyromazine, pymetrozine; triazolcarboxamides, such as, for example, triazamate, triazuron.

In the context of the present invention, it was found that combinations according to the invention comprising an active compound of group 1 and one or more active compounds from one of the substance classes mentioned above have a synergistically enhanced action, compared to the active compounds applied on their own.

Thus, the present invention provides in particular active compound combinations comprising at least one active compound from group 1 and at least one active compound from one or more of the above-defined substance classes of the carbamates, neonicotinoids, pyrazoles, macrolides, thiophosphates or dithiophosphates, or the pyrethroids or pyrethroid analogs.

Certain substance classes also have the same mechanism of action or the same site of action:

"Carbamates" and "thiophosphates" develop their neurotoxic action by inhibiting the enzyme acetylcholinesterase which plays an imminently important role in the conduction of nerve impulses: at a high reaction rate, it destroys the messenger acetylcholine which transmits the impulse from one neuron to another. If the enzyme is inhibited, acetylcholine accumulates and the entire neuronal system reaches a state of overexcitation.

The "neonicotinoids" are capable of docking to receptor molecules in the nervous system which normally accept acetylcholine, the messenger which transmits the impulse from one neuron to another. The active compounds block the acetylcholine receptors irreversibly and thus disturb decisively the physiological processes in the insect.

"Pyrethroids" or "pyrethroid analogs" delay the closure of the sodium channel on the plasma membrane of the nerve cell. Thus, the physiological process of repolarization and the establishment of a sufficiently negative resting membrane potential are inhibited. Moreover, they cause an elevated calcium concentration in the presynaptic neuron by inhibiting the calcium- and magnesium-dependent ATPase and the calcium-binding protein calmodulin. As a result, there is an increased release of neurotransmitters and an enhanced depolarization of the postsynaptic membrane. Finally, the pyrethroids inhibit the GABA-induced chloride influx. The latter is also observed with insecticides of the cyclodiene type.

"Pyrazoles", which are sometimes also referred to as "fibroles", act on the GABA (gamma-aminobutyric acid) receptor of the insects by preventing the passing of chloride ions, thus causing the collapse of the central nervous system. This mode of action also corresponds to that of cyclodienes.

"Benzoylureas" act during the larval stage of most insects by disturbing chitin biosynthesis. Typical effects are, for example, destruction or malformation of the cuticle.

Preference is furthermore given to active compound combinations as described above comprising at least one compound of the formula (I) in which X represents fluorine, chlorine or bromine and n represents 0 or 2.

Particular preference is furthermore given to active compound combinations as described above comprising at least one compound of the formula I) in which X represents fluorine or chlorine and n represents 2.

Especially preferred are active compound combinations as described above, comprising a compound of the formula (IA)

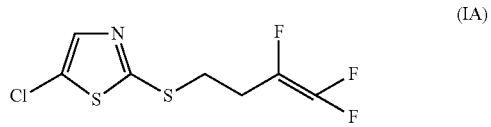 [SMILES: FC(F)=C(F)CCSc1ncc(Cl)s1]

and an active compound of group 2, preferably an active compound from the group consisting of aldicarb, alanycarb, aldoxycarb, aminocarb, bendiocarb, benfuracarb, BPMC, bufencarb, butocarboxim, carbaryl, carbofuran, carbosul fan, cloethocarb, ethiofencarb, fenobucarb, fenoxycarb, furathiocarb, isoprocarb, metam-sodium, methiocarb, methomyl, metolcarb, metolcarb, oxamyl, phosphocarb, pirimicarb, promecarb, propoxur, thiodicarb, thiofanox, trimethacarb, XMC, xylylcarb ("carbamates"), or an active compound from the group consisting of clothianidin, acetamiprid, AKD 1022, dinetofuran, imidacloprid, nitenpyram, thiacloprid, thiamethoxam ("neonicotinoid"), or an active compound from the group consisting of fipronil, acetoprole, ethiprole, fenpyroximate, vaniliprole ("pyrazoles"), or an active compound from the group consisting of spinosad, abamectin, avermectin, emamectin, emamectin-benzoate, ivermectin, milbemectin, milbemycin, moxidectin, thuringiensin "macrolides"), or an active compound from the group consisting of tebupirimfos, azamethiophos, azinphos-ethyl, azinphos-methyl, bromophos-ethyl, butathiofos, cadusafos, carbophenothion, chlorethoxyfos, chlorpyrifos, chlorpyrifos, chlorpyrifos-ethyl, chlorpyrifos-methyl, coumaphos, cyanophos, demeton, demeton-S-methyl, demeton-S-methyl-sulfone, dialifos, diazinon, dichlofenthion, dimethoate, disulfoton, ethion, ethoprophos, etrimfos, fenitrothion, fensulfothion, fenthion, flupyrazofos, fonofos, formothion, fosmethilan, iodofenphos, iprobenfos, isazofos, isoxathion, malathion, mecarbam, mesulfenfos, methacrifos, methidathion, omethoate, oxydemeton-methyl, parathion-methyl, phenthoate, phorate, phosalone, phosmet, phosphocarb, phoxim, pirimiphos-ethyl, pirimiphos-, methyl, profenofos, prothiofos, prothoate, pyraclofos, pyridaphenthion, pyridathion, quinalphos, sulfotep, sulprofos, temephos, terbufos, thiatriphos, thiometon, triazophos, vamidothion ("thiophosphates or "dithiophosphates"), or an active compound from the group consisting of tefluthrin, resmethrin, acrinathrin, allethrin (1R isomer), alpha-cypermethrin, beta-, cyfluthrin, beta-cypermethrin, bifenthrin, bioallethrin, bioallethrin (S-cyclopentyl isomer), bioethanomethrin, biopermethrin, bioresmethrin, brofenprox, chloethocarb, chlovaporthrin, cis-cypermethrin, cis-resmethrin, clocythrin, cycloprothrin, cyfluthrin, cyhalothrin, cypermethrin, cyphenothrin (1R-trans isomer), deltamethrin, dimefluthion, eflusilanate, empenthrin (1R isomer), esfenvalerate, etofenprox, fenfluthrin, fenpropathrin, fenpyrithrin, fenvalerate, flubrocythrinate, flubrocythrinate, flucythrinate, flufenprox, flufenprox, flumethrin, fluvalinate, fubfenprox, gamma-cyhalothrin, halfenprox, imiprothrin, kadethrin, lambda-cyhalothrin, metofluthrin, MIT-800, permethrin, phenothrin (1R-trans isomer), pralethrin, profluthrin, protrifenbute, pyresmethrin, pyrethrum, RU-12457, RU-15525, silafluofen, tau-fluvalinate, tetramethrin (1R isomer), theta-cypermethrin, tralocythrin, tralomethrin, transfluthrin, zeta-cypermethrin ("pyrethroids" and "pyrethroid analogs")

Especially preferred are active compound combinations as described above comprising a compound of the formula (IB)

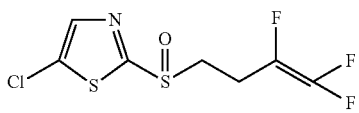

(IB)

and an active compound of group 2, preferably an active compound from the group consisting of alanycarb, aldicarb, aldoxycarb, aminocarb, bendiocarb, benfuracarb, BPMC, bufencarb, butocarboxim, carbaryl, carbofuran, carbosulfan, cloethocarb, ethiofencarb, fenobucarb, fenoxycarb, furathiocarb, isoprocarb, metam-sodium, methiocarb, methomyl, metolcarb, metolcarb, oxamyl, phosphocarb, pirimicarb, promecarb, propoxur, thiodicarb, thiofanox, trimethacarb, XMC, xylylcarb ("carbamates"), or an active compound from the group consisting of acetamiprid, AKD 1022, clothianidin, dinetofuran, imidacloprid, nitenpyram, thiacloprid, thiamethoxam ("neonicotinoids"), or an active compound from the group consisting of acetoprole, ethiprole, fenpyroximate, fipronil, vaniliprole ("pyrazoles"), or an active compound from the group consisting of abamectin, avermectin, emamectin, emamectin-benzoate, ivermectin, milbemectin, milbemycin, moxidectin, spinosad, thuringiensin ("macrolides"), or an active compound from the group consisting of azamethiophos, azinphos-ethyl, azinphos-methyl, bromophosethyl, butathiofos, cadusafos, carbophenothion, chlorethoxyfos, chlorpyrifos, chlorpyrifos, chlorpyrifos-ethyl, chlorpyrifos-methyl, coumaphos, cyanophos, demeton, demeton-S-methyl, demeton-S-methyl-sulfone, dialifos, diazinon, dichlofenthion, dimethoate, disulfoton, ethion, ethoprophos, etrimfos, fenitrothion, fensulfothion, fenthion, flupyrazofos, fonofos, formothion, fosmethilan, iodofenphos, iprobenfos, isazofos, soxathion, malathion, mecarbam, mesulfenfos, methacrifos, methidathion, omethoate, oxydemeton-methyl, parathion-methyl, phenthoate, phorate, phosalone, phosmet, phosphocarb, phoxim, pirimiphos-ethyl, pirimiphos-,methyl, profenofos, prothiofos, prothoate, pyraclofos, pyridaphenthion, pyridathion, quinalphos, sulfotep, sulprofos, tebupirimfos, temephos, terbufos, thiatriphos, thiometon, triazophos, vamidothion ("thiophosphates"), or an active compound from the group consisting of resmethrin, acrinathrin, allethrin (1R isomer), alpha-cypermethrin, beta-, cyfluthrin, beta-cypermethrin, bifenthrin, bioallethrin, bioallethrin (S-cyclopentyl isomer), bioethanomethrin, biopermethrin, bioresmethrin, brofenprox, chloethocarb, chlovaporthrin, cis-cypermethrin, cis-resmethrin, clocythrin, cycloprothrin, cyfluthrin, cyhalothrin, cypermethrin, cyphenothrin (1R-trans isomer), deltamethrin, dimefluthion, eflusilanate, empenthrin (1R-Isomer), esfenvalerate, etofenprox, fenfluthrin, fenpropathrin, fenpyrithrin, fenvalerate, flubrocythrinate, flubrocythrinate, flucythrinate, flufenprox, gamma-cyhalothrin, flufenprox, flumethrin, fluvalinate, fubfenprox, halfenprox, imiprothrin, kadethrin, lambda-cyhalothrin, metofluthrin, MIT-800, permethrin, phenothrin (1R-trans isomer), prallethrin, profluthrin, protrifenbute, pyresmethrin, pyrethrum, RU-12457, RU-15525, silafluofen, tau-fluvalinate, tefluthrin, tetramethrin (1R isomer), theta-cypermethrin, tralocythrin, tralomethrin, transfluthrin, zeta-cypermethrin ("pyrethroids" and "pyrethroid analogs").

Especially preferred are active compound combinations as described above comprising a compound of the formula (IC)

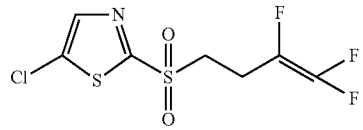

(IC)

and an active compound of group 2, preferably an active compound from the group consisting of alanycarb, aldicarb, aldoxycarb, aminocarb, bendiocarb, benfuracarb, BPMC, bufencarb, butocarboxim, carbaryl, carbofuran, carbosulfan, cloethocarb, ethiofencarb, fenobucarb, fenoxycarb, furathiocarb, isoprocarb, metam-sodium, methiocarb, methomyl, metolcarb, metolcarb, oxamyl, phosphocarb, pirimicarb, promecarb, propoxur, thiodicarb, thiofanox, trimethacarb, XMC, xylylcarb ("carbamates"), or an active compound from the group consisting of acetamiprid, AKD 1022, clothianidin, dinetofuran, imidacloprid, nitenpyram, thiacloprid, thiamethoxam ("neonicotinoids"), or an active compound from the group consisting of acetoprole, ethiprole, fenpyroximate, fipronil, vaniliprole ("pyrazoles"), or an active compound from the group consisting of abamectin, avermectin, emamectin, emamectin-benzoate, ivermectin, milbemectin, milbemycin, moxidectin, spinosad, thuringiensin ("macrolides"), or an active compound from the group consisting of azamethiophos, azinphos-ethyl, azinphos-methyl, bromophosethyl, butathiofos, cadusafos, carbophenothion, chlorethoxyfos, chlorpyrifos, chlorpyrifos, chlorpyrifos-ethyl, chlorpyrifos-methyl, coumaphos, cyanophos, demeton, demeton-S-methyl, demeton-S-methyl-sulfone, dialifos, diazinon, dichlofenthion, dimethoate, disulfoton, ethion, ethoprophos, etrimfos, fenitrothion, fensulfothion, fenthion, flupyrazofos, fonofos, formothion, fosmethilan, iodofenphos, iprobenfos, isazofos, isoxathion, malathion, mecarbam, mesulfenfos, methacrifos, methidathion, omethoate, oxydemeton-methyl, parathion-methyl, phenthoate, phorate, phosalone, phosmet, phosphocarb, phoxim, pirimiphos-ethyl, pirimiphos-, methyl, profenofos, prothiofos, prothoate, pyraclofos, pyridaphenthion, pyridathion, quinalphos, sulfotep, sulprofos, tebupirimfos, temephos, terbufos, thiatriphos, thiometon, triazophos, vamidothion ("thiophosphates or "dithiophosphates"), or an active compound from the group consisting of resmethrin, acrinathrin, allethrin (1R isomer), alpha-cypermethrin, beta-, cyfluthrin, beta-cypermethrin, bifenthrin, bioallethrin, bioallethrin (S-cyclopentyl isomer), bioethanomethrin, biopermethrin, bioresmethrin, brofenprox, chloethocarb, chlovaporthrin, cis-cypermethrin, cis-resmethrin, clocythrin, cycloprothrin, cyfluthrin, cyhalothrin, cypermethrin, cyphenothrin (1R-trans isomer), deltamethrin, dimefluthion, eflusilanate, empenthrin (1R isomer), esfenvalerate, etofenprox, fenfluthrin, fenpropathrin, fenpyrithrin, fenvalerate, flubrocythrinate, flubrocythrinate, flucythrinate, flufenprox, flufenprox, flumethrin, fluvalinate, fubfenprox, gamma-cyhalothrin, halfenprox, imiprothrin, kadethrin, lambda-cyhalothrin, metofluthrin, MIT-800, permethrin, phenothrin (1R-trans isomer), prallethrin, profluthrin, protrifenbute, pyresmethrin, pyrethrum, RU-12457, RU-15525, silafluofen, tau-fluvalinate, tefluthrin, tetramethrin (1R isomer), theta-cypermethrin, tralocythrin, tralomethrin, transfluthrin, zeta-cypermethrin ("pyrethroids" and "pyrethroid analogs").

Particularly preferred combinations according to the invention are shown in the table below.

TABLE 1

| Active compound of group 1 | Active compound of group 2 |
|---|---|
| (IA) | aldicarb |
| (IB) | aldicarb |
| (IC) | aidicarb |
| (IA) | clothianidin |
| (IB) | clothianidin |
| (IC) | clothianidin |
| (IA) | fipronil |
| (IB) | fipronil |
| (IC) | fipronil |
| (IA) | imidacloprid |
| (IB) | imidacloprid |
| (IC) | imidacioprid |
| (IA) | spinosad |
| (IB) | spinosad |
| (IC) | spinosad |
| (IA) | tebupirimfos |
| (IB) | tebupirimfos |
| (IC) | tebupirimfos |
| (IA) | tefluthrin |
| (IB) | tefluthrin |
| (IC) | tefluthrin |
| (IA) | (IIA) |
| (IB) | (IIA) |
| (IC) | (IIA) |
| (IA) | chlorethoxyfos |
| (IB) | chlorethoxyfos |
| (IC) | chlorethoxyfos |
| (IA) | ethiprole |
| (IB) | ethiprole |
| (IC) | ethiprole |
| (IA) | thiamethoxam |
| (IB) | thiamethoxam |
| (IC) | thiamethoxam |
| (IA) | carbofuran |
| (IB) | carbofuran |
| (IC) | carbofuran |
| (IA) | terbufos |
| (IB) | terbufos |
| (IC) | terbufos |
| (IA) | carbosulfan |
| (IB) | carbosulfan |
| (IC) | carbosulfan |
| (IA) | furathiocarb |
| (IB) | furathiocarb |
| (IC) | furathiocarb |
| (IA) | cadusafos |
| (IB) | cadusafos |
| (IC) | cadusafos |

In addition, the active compound combinations may also comprise other fungicidally, acaricidally or insecticidally active components which may be admixed.

If the active compounds are present in the active compound combinations according to the invention in certain weight ratios, the synergistic effect is particularly pronounced. However, the weight ratios of the active compounds in the active compound combinations may be varied within a relatively wide range. In general, the combinations according to the invention comprise active compounds of the formula (I) and the co-component in the preferred mixing ratios indicated in the table below, the mixing ratios being based on weight ratios. The ratio is to be understood as meaning active compound of formula (I):co-component

TABLE 2

| Preferred mixing ratio |
|---|
| 2:1 to 1:1000 |
| 10:1 to 1:10 |
| 20:1 to 1:5 |
| 50:1 to 1:5 |
| 100:1 to 1:5 |
| 1000:1 to 1:2 |

The active compound combinations according to the invention are suitable for controlling animal pests, preferably arthropods and nematodes, in particular nematodes and insects found in agriculture, in animal health, in forests, in the protection of stored products and materials and in the hygiene sector. They are active against normally sensitive and resistant species, and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomo-*

*nella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hyleinyia* spp., *Liriomyza* spp.

From the order of the Siphonaptera, for example, *Xenopsylla cheopis, Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonenius* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

The active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics and chlorinated aliphatic hydrocarbons such as chlorobenzenes, chloroethylenes and methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Suitable solid carriers are:

for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, corn cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates; suitable dispersants are: for example lignin-sulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use loans.

When used against hygiene pests and stored-product pests, the active compound combinations are distinguished by an excellent residual action on wood and clay as well as good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, hair lice, bird lice and fleas. These parasites include:

From the order of the Anopiurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattella germanica, Supella* spp.

From the subclass of the Acaria (Acarida) and the order of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combinations according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising molded articles such as collars, ear tags, tail tags, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10 000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:

Beetles such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus*.

Dermapterans such as *Sirex juvencus, Urocerus gigas, Urocerus gigas taignus, Urocerus augur*.

Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus*.

Bristle-tails such as *Lepisma saccharina*.

Industrial materials in the present context are understood as meaning non-living materials such as, preferably, polymers, adhesives, glues, paper and board, leather, wood, timber products and paints.

The material which is to be protected from insect attack is very especially preferably wood and timber products.

Wood and timber products which can be protected by the composition according to the invention, or mixtures comprising it, are to be understood as meaning, for example: construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of turpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution, Bitumen or bituminous substances may also be used as binders, in amounts of up to 10% by weight. In addition, colorants, pigments, water repellants, odor-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di(2-ethylhexyl)adipate, stearates such as butyl stearate or amyl stearate, oleates such as butyl oleate, glycerol ethers or higher-molecular-weight glycol ethers, glycerol esters and p-toluenesulfonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The active compound combinations according to the invention can at the same time be employed for protecting objects which come into contact with saltwater or brackish water, such as hulls, screens, nets, buildings, moorings and signaling systems, against fouling.

Fouling by sessile Oligochaeta, such as Serpulidae, and by shells and species from the Ledamorpha group (goose barnacles), such as various *Lepas* and *Scalpelum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the active compound combinations according to the invention have an outstanding antifouling action.

Using the active compound combinations according to the invention, allows the use of heavy metals such as, for example, in bis(trialkyltin) sulfides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl(bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propynyl butylcarbamate, tolylfluanid and azoles such as, for example, azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb;

or conventional antifouling active compounds such as 4,5-dichloro-2-octyl-4-isothiazolin-3-one, diiodomethylparatryl sulfone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulfonyl) pyridine, 2,4,5,6-tetrachloroisophthalonitrile, tetramethylthiuram disulfide and 2,4,6-trichlorophenylmaleiimide.

The antifouling compositions used comprise the active compound combinations according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in saltwater. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephaia, Chrysozona pluvialis, Culex quinquefaseiatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramoriuni caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and genetic engineering or by combinations of these methods, inclusive of the transgenic plants and inclusive of the plant varieties protectable or not protectable by plant breeders' rights. Plant pans are to be understood as meaning all above-ground and below-ground parts and organs of plants, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seed, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetic Modified Organisms), and parts thereof are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred and to be treated according to the invention include all plants which, in the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), corn, soybeans, potatoes, cotton, oilseed rape and also fruit plants (with the fruits apples, pears, citrus fruits and grapevines), and particular emphasis is given to corn, soybeans, potatoes, cotton and oilseed rape. Traits that are particularly emphasized are increased defense of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulfonylureas, glyphosate or phosphinotricin (for example the "PAT" gene). The genes which impart the desired traits in question can also be present in combination with one another in the transgenic plants. Examples of "Bt plants" which may be mentioned are corn Cultivars, cotton cultivars, soybean cultivars and potato cultivars which are sold under the trade names YIELD GARD® (for example corn, cotton, soybeans), KnockOut® (for example corn), Star-Link® (for example corn), Bollgard® (cotton), Nucotn® (cotton) and NewLeaf® (potato). Examples of herbicide-tolerant plants which may be mentioned are corn cultivars, cotton cultivars and soybean cultivars which are sold under the trade names Roundup Ready® (tolerance to glyphosate, for example corn, cotton, soybean), Liberty Link® (tolerance to phosphinotricin, for example oilseed rape), IMI® (tolerance to imidazolinones) and STS® (tolerance to sulfonylurea, for example corn). Herbicide-resistant plants (plants bred in a conventional manner for herbicide tolerance) which may be mentioned include the cultivars sold under the name Clearfield® (for example corn). Of course, these statements also apply to plant cultivars having these or still to be developed genetic traits, which plants will be developed and/or marketed in the future.

The plants listed can be treated according to the invention in a particularly advantageous manner with the active compound mixtures according to the invention. The preferred ranges stated above for the mixtures also apply to the treatment of these plants. Particular emphasis is given to the treatment of plants with the mixtures specifically mentioned in the present text.

The good insecticidal and acaricidal action of the active compound combinations according to the invention can be seen from the examples which follow. While the individual active compounds show weaknesses in their action, the combinations show an action which exceeds a simple sum of actions.

A synergistic effect is always present when the action of the active compound combinations exceeds the total of the actions of the active compounds when applied individually.

The expected action for a given combination of two active compounds can be calculated as follows, using the formula of S. R. Colby, Weeds 15 (1967), 20-22:

If

X is the kill rate, expressed as % of the untreated control, when employing active compound A at an application rate of m g/ha or in a concentration of m ppm, Y is the kill rate, expressed as % of the untreated control, when employing active compound B at an application rate of n g/ha or in a concentration of n ppm and E is the kill rate, expressed as % of the untreated control, when employing active compounds A and B at application rates of m and n g/ha or in a concentration of m and n ppm, then $$E = X + Y - \frac{X \cdot Y}{100}$$

If the actual insecticidal kill rate exceeds the calculated value, the kill action of the combination is superadditive, i.e. a synergistic effect is present. In this case, the actually observed kill rate must exceed the value calculated using the above formula for the expected kill rate (E).

EXAMPLES

Example A

*Phaedon*-Larvae Test

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist. After the desired period of time, the kill in percent is determined. 100% means that all beetle larvae have been killed; 0% means that none of the beetle larvae has been killed. The kill rates determined are inserted into Colby's formula (see sheet 34).

In this test, the following active compound combination in accordance with the present application showed a synergistically enhanced activity compared to the active compounds applied on their own (found*=activity found in the test; calc.**=activity calculated according to Colby):

TABLE 3

| (IC) + tefluthrin | | |
|---|---|---|
| Active compound | Active compound concentration [ppm] | Kill rate [%] after 3 days |
| (IC) | 500 | 0 |
| tefluthrin | 4 | 75 |
| (IC) + tefluthrin (125:1) | 500 + 4 | found*: 100 calc.**: 75 |

TABLE 4

| (IC) + aldicarb | | |
|---|---|---|
| Active compound | Active compound concentration [ppm] | Kill rate [%] after 3 days |
| (IC) | 500 | 0 |
| aldicarb | 20 | 35 |
| (IC) + aldicarb (25:1) | 500 + 20 | found*: 75 calc.**: 35 |

TABLE 5

| (IC) + clothianidin | | |
|---|---|---|
| Active compound | Active compound concentration [ppm] | Kill rate [%] after 3 days |
| (IC) | 500 | 0 |
| clothianidin | 4 | 15 |
| (IC) + clothianidin (125:1) | 500 + 4 | found*: 75 calc.**: 15 |

TABLE 6

| (IC) + imidacloprid | | |
|---|---|---|
| Active compound | Active compound concentration [ppm] | Kill rate [%] after 3 days |
| (IC) | 500 | 0 |
| imidacloprid | 20 | 45 |
| (IC) + imidacloprid (25:1) | 500 + 20 | found*: 80 calc.**: 45 |

Example B

*Plutella* Test, Sensitive Strain

Solvent: 7 parts by weight of dimethylformamide
Emulsifier: 2 parts by weight of alkylaryl polyglycol ether To produce a suitable preparation of active compound, 1 part by weight of active compound is mixed with the stated amounts of solvent and emulsifier, and the concentrate is diluted with emulsifier containing water to the desired concentration.

Cabbage leaves (*Brassica oleracea*) are treated by being dipped into the preparation of active compound of the desired concentration and are populated with caterpillars of the diamondback moth (*Plutella xylostella*, sensitive strain) while the leaves are still moist. After the desired period of time, the kill in percent is determined. 100% means that all caterpillars have been killed; 0% means that none of the caterpillars has been killed. The kill rates determined are inserted into Colby's formula (see sheet 34).

In this test, the following active compound combination in accordance with the present application showed a synergistically enhanced activity compared to the active compounds applied on their own (found*=activity found in the test; calc.**=activity calculated according to Colby):

TABLE 7

(IC) + tefluthrin

| Active compound | Active compound concentration [ppm] | Kill rate [%] after 3 days |
|---|---|---|
| (IC) | 500 | 0 |
| tefluthrin | 0.16 | 20 |
| (IC) + tefluthrin (3125:1) | 500 + 0.16 | found*: 65 calc.**: 20 |

TABLE 8

(IC) + aldicarb

| Active compound | Active compound concentration [ppm] | Kill rate [%] after 6 days |
|---|---|---|
| (IC) | 500 | 20 |
| aldicarb | 20 | 0 |
| (IC) + aldicarb (25:1) | 500 + 20 | found*: 50 calc.**: 20 |

TABLE 9

(IC) + imidacloprid

| Active compound | Active compound concentration [ppm] | Kill rate [%] after 6 days |
|---|---|---|
| (IC) | 500 | 0 |
| imidacloprid | 20 | 5 |
| (IC) + imidacloprid (25:1) | 500 + 20 | found*: 65 calc.**: 5 |

TABLE 10

(IC) + tebupirimfos

| Active compound | Active compound concentration [ppm] | Kill rate [%] after 3 days |
|---|---|---|
| (IC) | 500 | 5 |
| tebupirimfos | 0.8 | 0 |
| (IC) + tebupirimfos (625:1) | 500 + 0.8 | found*: 40 calc.**: 5 |

TABLE 11

(IC) + (IIA)

| Active compound | Active compound concentration [ppm] | Kill rate [%] after 3 days |
|---|---|---|
| (IC) | 500 | 5 |
| (IIA) | 4 | 95 |
| (IC) + (IIA) (125:1) | 500 + 4 | found*: 100 calc.**: 95.25 |

Example C

*Spodoptera frugiperda* Test
Solvent: 7 parts by weight of dimethylformamide
Emulsifier: 2 parts by weight of alkylaryl polyglycol ether
To produce a suitable preparation of active compound, 1 part by weight of active compound is mixed with the stated amounts of solvent and emulsifier, and the concentrate is diluted with emulsifier containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist. After the desired period of time, the kill in percent is determined. 100% means that all caterpillars have been killed; 0% means that none of the caterpillars has been killed. The kill rates determined are inserted into Colby's formula (see sheet 34).

In this test, the following active compound combination in accordance with the present application showed a synergistically enhanced activity compared to the active compounds applied on their own (found*=activity found in the test; calc.**=activity calculated according to Colby):

TABLE 12

(IC) + tefluthrin

| Active compound | Active compound concentration [ppm] | Kill rate [%] after 3 days |
|---|---|---|
| (IC) | 500 | 0 |
| tefluthrin | 0.8 | 40 |
| (IC) + tefluthrin (625:1) | 500 + 0.8 | found*: 100 calc.**: 40 |

TABLE 13

(IC) + spinosad

| Active compound | Active compound concentration [ppm] | Kill rate [%] after 3 days |
|---|---|---|
| (IC) | 500 | 0 |
| spinosad | 0.16 | 60 |
| (IC) + spinosad (3125:1) | 500 + 0.16 | found*: 95 calc.**: 60 |

TABLE 14

(IC) + clothianidin

| Active compound | Active compound concentration [ppm] | Kill rate [%] after 3 days |
|---|---|---|
| (IC) | 500 | 0 |
| clothianidin | 4 | 85 |
| (IC) + clothianidin (125:1) | 500 + 4 | found*: 100 calc.**: 85 |

TABLE 15

(IC) + fipronil

| Active compound | Active compound concentration [ppm] | Kill rate [%] after 6 days |
|---|---|---|
| (IC) | 500 | 20 |
| fipronil | 0.8 | 0 |
| (IC) + fipronil (625:1) | 500 + 0.8 | found*: 55 calc.**: 20 |

TABLE 16

| | (IC) + tebupirimfos | |
|---|---|---|
| Active compound | Active compound concentration [ppm] | Kill rate [%] after 6 days |
| (IC) | 500 | 20 |
| tebupirimfos | 0.8 | 0 |
| (IC) + tebupirimfos (625:1) | 500 + 0.8 | found*: 45 calc.**: 20 |

TABLE 17

| | (IC) + (IIA) | |
|---|---|---|
| Active compound | Active compound concentration [ppm] | Kill rate [%] after 6 days |
| (IC) | 500 | 20 |
| (IIA) | 100 | 30 |
| (IC) + (IIA) (5:1) | 500 + 100 | found*: 85 calc.**: 44 |

Example D

*Myzus* Test
Solvent: 7 parts by weight of dimethylformamide
Emulsifier: 2 parts by weight of alkylaryl polyglycol ether
To produce a suitable preparation of active compound, 1 part by weight of active compound is mixed with the stated amounts of solvent and emulsifier, and the concentrate is diluted with emulsifier containing water to the desired concentration.

Cabbage leaves (*Brassica oleracea*), which are heavily infested by the green peach aphid (*Myzus persicae*) are treated by being dipped into the preparation of active compound of the desired concentration. After the desired period of time, the kill in % is determined. 100% means that all aphids have been killed; 0% means that none of the aphids has been killed. The kill rates determined are inserted into Colby's formula (see sheet 1).

In this test, the following active compound combination in accordance with the present application showed a synergistically enhanced activity compared to the active compounds applied on their own (found*=activity found in the test; calc.**=activity calculated according to Colby):

TABLE 18

| | (IC) + tefluthrin | |
|---|---|---|
| Active compound | Active compound concentration [ppm] | Kill rate [%] after 1 day |
| (IC) | 100 | 0 |
| tefluthrin | 4 | 0 |
| (IC) + tefluthrin (25:1) | 100 + 4 | found*: 30 calc.**: 0 |

TABLE 19

| | (IC) + tebupirimfos | |
|---|---|---|
| Active compound | Active compound concentration [ppm] | Kill rate [%] after 6 days |
| (IC) | 100 | 0 |
| tebupirimfos | 20 | 35 |

TABLE 19-continued

| | (IC) + tebupirimfos | |
|---|---|---|
| Active compound | Active compound concentration [ppm] | Kill rate [%] after 6 days |
| (IC) + tebupirimfos (5:1) | 100 + 20 | found*: 80 calc.**: 35 |

TABLE 20

| | (IC) + (IIA) | |
|---|---|---|
| Active compound | Active compound concentration [ppm] | Kill rate [%] after 6 days |
| (IC) | 100 | 0 |
| (IIA) | 4 | 55 |
| (IC) + (IIA) (25:1) | 100 + 4 | found*: 65 calc.**: 55 |

The invention claimed is:
1. A synergistic active pesticidal composition, characterized in that it comprises an active pesticidal compound combination comprising:
(A) one or more active pesticide compounds of group 1 having the formula (I)

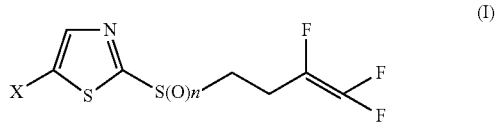

in which
X represents halogen, and
n is 0, 1 or 2,
and
(b) one or more active pesticide compounds of group 2 selected from members of groups (b1) through (b7) consisting of:
(b1) alanycarb, aldoxycarb, aminocarb, bendiocarb, benfuracarb, BPMC, bufencarb, butocarboxim, carbaryl, carbofuran, carbosulfan, cloethocarb, ethiofencarb, fenobucarb, fenoxycarb, furathiocarb, isoprocarb, metam-sodium, methiocarb, methomyl, metolcarb, metolearb, oxamyl, phosphocarb, pirimicarb, promecarb, propoxur, thiodicarb, thiofanox, trimethacarb, XMC, xylylcarb;
(b2) acetamiprid, AKD 1022, dinetofuran, nitenpyram, thiacloprid, thiamethoxam;
(b3) acetoprole, ethiprole, fenpyroximate, vaniliprole;
(b4) avermectin, ivermectin, milbemectin, milbemycin, moxidectin, thuringiensin;
(b5) azamethiophos, azinphos-ethyl, azinphos-methyl, bromophos-ethyl, butathiofos, cadusafos, carbophenothion, chlorethoxyfos, chlorpyrifos, chlrpyrifos, chlorpyrifos-ethyl, chlorpyrifos-methyl, coumaphos, cyanophos, demeton, demeton-S-methyl, demeton-S-methyl-sulfone, dialifos, diazinon, dichlofenthion, dimethoate, disulfoton, ethion, ethoprophos, etrimfos, fenitrothion, fensulfothion, fenthion, flupyrazofos, fonofos, formothion, fosmethilan, iodofenphos, iprobenfos, isazofos, isoxathion, malathion, mecarbam, mesulfenfos, methacrifos, methidathion, omethoate, oxydemeton-methyl, parathion-methyl, phenthoate, phorate, phosalone, phosmet, phosphocarb, phoxim, pirimiphos-ethyl, pirimiphos-methyl, profenofos, prothiofos, prothoate, pyraclofos, pyridaphenthion, pyridathion, quinalphos, sulfotep, sulprofos, temephos, terbufos, thiatriphos, thiometon, triazophos, vamidothion;

(B6) resmethrin, acrinathrin, allethrin (1R isomer), alphacypermethrin, beta-cyfluthrin, beta-cypermethrin, bifenthrin, bioallethrin, bioallethrin (S-cyclopentyl isomer), bioethanomethrin, biopermethrin, bioresmethrin, brofenprox, chloethocarb, chlovaporthrin, cis-cyperrnethrin, cis-resmethrin, clocythrin, cycloprothrin, cyfluthrin, cyhalothrin, cypermethrin, cyphenothrin (1R-trans isomer), deltamethrin, dimefluthrin, eflusilanate, empenthrin (1R isomer), esfenvalerate, etofenprox, fenfluthrin, fenpropathrin, fenpyrithrin, fenvalerate, flubrocythrinate, flubrocythrinate, flucythrinate, flufenprox, flumethrin, fluvalinate, fubfenprox, gammacyhalothrin, halfenprox, imiprothrin, kadethrin, lambda-cyhalothrin, metofluthrin, MIT-800, permethrin, phenothrin (1R-trans isomer), prallethrin, profluthrin, protrifenbute, pyresmethrin, pyrethrum, RU-12457, RU-15525, silafluofen, taufluvalinate, tetramethrin (1R isomer), theta-cypermethrin, tralocythrin, tralomethrin, transfluthrin, and zeta-cypermethrin.

2. The composition of claim 1, characterized in that it comprises one or more active pesticide compounds of formula (I) in which X represents fluorine, chlorine or bromine, and n is 0 or 2.

3. The composition of claim 1, characterized in that it comprises one or more active pesticide compounds of formula (I) in which X represents fluorine or chlorine, and n represents 2.

4. The composition of claim 1, characterized in that it comprises, as active pesticide compounds of group 1, one or more of the compounds of formula (IA), (IB) or (IC)

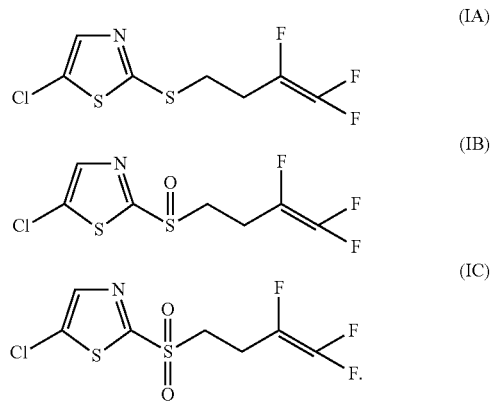

5. The composition of claim 1, characterized in that it comprises, as active pesticide compound of group 1, the compounds of formula (IC).

6. A method of controlling pests, comprising contacting a composition of claim 1 with the pest or the habitat of the pest.

7. A process for producing synergistic compositions, comprising mixing the composition of claim 1 with surfactants and/or extenders.

* * * * *